US006197738B1

(12) United States Patent
Regutti

(10) Patent No.: US 6,197,738 B1
(45) Date of Patent: Mar. 6, 2001

(54) NONTOXIC SANITIZING CLEANSER BASED ON ORGANIC ACIDS AND METHODS OF USING SAME

(76) Inventor: Robert R. Regutti, 410 N. Dunlap Ave., Viroqua, WI (US) 54665

( * ) Notice: Subject to any disclaimer, the term of this patent is extended or adjusted under 35 U.S.C. 154(b) by 0 days.

(21) Appl. No.: 08/846,415

(22) Filed: Apr. 30, 1997

Related U.S. Application Data

(63) Continuation-in-part of application No. 07/790,183, filed on Nov. 12, 1991, now abandoned, which is a continuation-in-part of application No. 07/561,799, filed on Aug. 2, 1990, now abandoned.

(51) Int. Cl.[7] .................................. C11D 3/48; C11D 7/08
(52) U.S. Cl. .......................... 510/383; 510/218; 510/219; 510/234; 510/426; 510/427; 510/428; 510/434; 510/477; 510/480; 510/495; 510/498; 510/131; 134/3; 134/22.1; 134/22.13; 134/22.14; 134/22.16; 134/22.17; 134/22.19; 134/34; 134/39; 134/40; 134/41; 134/42
(58) Field of Search ...................................... 510/218, 219, 510/234, 383, 426, 427, 428, 434, 477, 480, 495, 498, 131; 134/3, 22.1, 22.13, 22.14, 22.16, 22.17, 22.19, 34, 39–42

(56) References Cited

U.S. PATENT DOCUMENTS 3,211,659 * 10/1965 Pikaar .................................. 510/111
4,749,508 * 6/1988 Cockrell, Jr. et al. ............... 510/201

FOREIGN PATENT DOCUMENTS

93/09213 * 12/1993 (WO) .

OTHER PUBLICATIONS

"Indirect food additives: adjuvants, production aids, and sanitizers" in Federal Register (1995), 60(71), 18739–40, Apr. 13, 1995.*
"Antimicrobial Efficacy of a New Organic Acid Anionic Surfactant Against Various Bacterial Strains", Restaino et al., Journal of Food Protection, vol. 57, No. 6, pp. 496–501, Jun. 1994.*
"Introducing GYCOR's New Multi–Purpose Sanitizer Gycorine™" brochure, 1995.*

* cited by examiner

Primary Examiner—Mark Kopec
Assistant Examiner—Brian P. Mruk
(74) Attorney, Agent, or Firm—Marshall A. Burmeister

(57) ABSTRACT

A nontoxic sanitizing cleaner comprising an organic acid having a pH less than 3, a chelating agent, and a surfactant. The invention also contemplates a buffering agent in the cleaner. In a preferred embodiment, the sanitizing cleanser is in the form of a solution containing 94% citric acid, 4% EDTA, 1% sodium laurel sulfate, and 1% monosodium phosphate, by weight.

The invention also contemplates using the nontoxic sanitizing cleaner in a cosmetic lotion, and in processes for cleaning and sanitizing food processing equipment.

21 Claims, No Drawings

NONTOXIC SANITIZING CLEANSER BASED ON ORGANIC ACIDS AND METHODS OF USING SAME

This application is a continuation-in part of application Ser. No. 07/790,183 filed Nov. 12, 1991, now abandoned, which is a continuation-in-part of abandoned application Ser. No. 07/561,799 filed Aug. 2, 1990, now abandoned. The present invention relates to antimicrobial preparations which are capable of cleaning surfaces.

BACKGROUND OF THE INVENTION

There are many applications which require the application of a sanitizing preparation to a surface to prevent buildup of microorganisms on the surface and consequent health threats. One such application is cleaning and sanitizing processing equipment, and counters and tables which are in contact with food, such as in restaurants. Another application is disinfecting and cleaning surfaces in hospitals and health care facilities. Also, a sanitizing preparation is desired to remove microorganisms from the skin of a person by applying the preparation in the form of a lotion, ointment or salve directly to the skin.

In such applications, it is desirable to kill the microorganisms on the surfaces and thereafter remove the remnants of the organism by a cleaning process. In the past, most sanitizing preparations have killing power, but little cleaning power. Further, the sanitizing preparations used in the past generally contain caustic or toxic ingredients and must be washed off with water, or isolated from the skin of the person applying it, such as with gloves. The commonly used sanitizing preparations are based on chlorine, iodine, or quaternary compounds, and require care in applying the preparation and present a storage and health hazard.

It is an object of the present invention to provide a sanitizing preparation which may be applied by hand and will not harm the skin of the person applying the preparation. It is also an object of the present invention to provide a sanitizing preparation which may be applied to the skin of a person to remove microorganisms from the skin. Further, it is an object of the invention to provide such a sanitizing preparation which is more effective than bleach in destroying the most important disease producing microorganisms In addition, it is an object of the present invention to provide a sanitizing preparation which not only effectively destroys microorganisms, but also is an effective surface cleaner without the need of a water rinse.

SUMMARY OF THE INVENTION

It has long been known that microorganisms are inhibited by an acidic atmospheres Accordingly, an organic acid with a pH less than three is utilized as an ingredient of the preparation according to the present invention. While organic acids, such as citric acid, retard the growth of microorganisms, they have not been noted for the rapid destruction of such organisms.

The inventor has found that the direct kill rate of certain important bacterial organisms is increased by applying a preparation to such surfaces which adds a chelating agent to the organic acid. Further, the direct kill rate of the preparation is further increased to exceed that of chlorine by the addition of a surfactant. In addition, a preparation with an organic acid, chelating agent and surfactant functions as an effective cleaning agent. Further, the inventor has found that the ingredients of this composition may be selected of noncaustic and nontoxic materials, and the resulting sanitizing cleaner is itself noncaustic and nontoxic.

The organic acid must have a pH less than three, and creates an inhospitable environment for microorganisms. Not all microorganisms will be killed by the organic acid alone, and the addition of a chelating agent expands the organisms that will be killed by the composition and increases the kill rate. It is believed that the chelating agent functions by tying up the metals and making them unavailable to the microorganism. Microorganisms require metals to carry out normal functions, and the effect of the chelating agent is believed to starve the microorganisms and destroy them.

The preparation utilizes a surfactant to wet the surfaces that are subjected to the preparation and facilitate cleaning of those surfaces. The surfactant not only facilitates use of the preparation as a cleaner, but it also affects the kill rate of microorganisms. It is believed that the surfactant effects the outer protective membrane of the microorganism, and creates openings for the entry of the preparation into the microorganism to expedite the reaction of the ingredients of the preparation on the microorganism. It is further believed that the surfactant causes the microorganism to leak protoplasm, thus reducing its defenses and impeding its ability to reproduce.

The inventor has also found that the kill rate can be increased by the addition of a buffering agent to the preparation. It is believed that the buffering agent maintains the hydrogen potential of the composition constant, thus accelerating the reaction of the preparation.

Organic acids are available which also have a chelating function, although a weaker function than available chelating agents. Also, surfactants are available which have a chelating function, although a weak function. It is thus possible to optimize the chelating function by selecting an organic acid and surfactant which will contribute to the chelating function.

Water may be added to the preparation to form a solution, and it has been found that a highly dilute solution of a preparation consisting of about 85% to 98% of an organic acid, about 0.2% to about 10% of a chelating agent, and about 0.2% to about 5% of a surfactant, by weight, will function as a sanitizing cleaners. A solution of between about 0.2% and 5% of the preparation to between about 99.8% to 95% water by weight has been found to be effective. The solution will be more effective with a preparation containing between about 0.2% to about 5% of a buffering agent by weight.

The preparation may also be combined with a lotion and used as a hand cleaner. A water based lotion is particularly desirable since it also functions as a moisturizer. A combination of as little as about 1% of the preparation to about 99% water based lotion has been found to produce a sanitizing and cleaning lotion which also moisturizes the skin.

DESCRIPTION OF THE DRAWING

There is no drawing.

DESCRIPTION OF THE PREFERRED EMBODIMENT

Among the organic acids that are useful in the preparation, citric acid has been preferred for use in the applications set forth above. Other organic acids which are suitable for practicing the invention are fumaric acid, tartaric acid, malic acid, lactic acid, and adipic acid, and mixtures of the enumerated acids.

Among the chelating agents that are suitable for use in the preparation of the invention, ethylene-diaminetetraacetic acid, known as EDTA, and its salts, particularly its sodium and potassium salts, are preferred. Other chelating agents suitable for practicing the invention are salicylic acid, polyphosphates, ascorbicacid and blends of these enumerated chelating agents. Even citric acid, a hydroxypolycarboxylic acid, acts as a chelating agent in this nontoxic sanitizing cleaner.

The preparation requires an anionic surfactant, and the preferred surfactants are sodium lauryl sulfate or ammonium lauryl sulfate. Other suitable surfactants for practicing the invention are the sarcosinates, particularly sodium lauryl sarcosinate, the sulfoacetates, particularly sodium lauryl sulfoacetate, the sulfosuccinates, particularly disodium monoaleanida or laureth sulfosuccinate, or blends of the enumerated surfactants.

The inventor has found monosodium or potassium phosphate, or mixtures thereof to be the preferred buffering agents. The buffering agent should have a pH less than about 5.

In the preferred embodiment of the present invention, the preparation is a mixture of citric acid, ethylenediaminetetraacetic acid (EDTA) or its salts, sodium lauryl sulfate and monosodium phosphate. This preparation has been found to be very effective against pseudomonas, staphylococcus and salmonella, as well as the saccharomyces bailii yeast. It is believed that one of the reasons for the effectiveness of this preparation is the fact that citric acid and sodium lauryl sulfate both function as mild chelating agents, and the chelating effect of these ingredients is additive with that of EDTA and/or its salts.

The organic acid must be sufficiently acidic to produce a pH for the preparation as a whole less than 3, and preferably in the range of 2.0 to 2.3. In a preferred example of the present invention, the organic acid is citric acid having a formula $C_6H_8O_7$ obtained in anhydrouscrystalline form. The chelating agent is EDTA or its salts, also known as ethylenediaminetetraacetic acid, marketed by W. R. Grace & Co. under the name HAMP-ENE EDTA or its salts (HAMP-ENE ii Na(2) or Na(4), etc.). All EDTA forms are obtainable in crystalline powder form. The surfactant is sodium lauryl sulfate obtained from Stepan Distributors under the trade name STEPANOL ME-DRY. The sodium lauryl sulfate is obtained in dry powder form. The buffering agent is monosodium phosphate with a formula $NaH_2PO_4$. The monosodium phosphate is obtained in dry powder form from Harcros Chemicals, Inc. under the trade name PHOS SODA MONO ANHY GRAN.

In one of the preferred preparations, citric acid constitutes 85% to 98% of the dry preparation, EDTA or its salts constitutes 0.2% to 10% of the dry preparation, and sodium lauryl sulfate constitutes 0.2% to 5% of the preparation by weight. The preferred buffering agent for use in the preparation is monosodium phosphate, and the monosodium phosphate constitutes 0.2% to 5% of the preparation by weight. The dry ingredients are dissolved in water, preferably deionized water, and the proportion of the dry preparation to water is between 0.3% and 5% preparation to between 95% and 99.7% water, by weight.

EXAMPLE 1

A dry mixture of citric acid, EDTA (disodium), sodium lauryl sulfate and monosodium phosphate, in the proportions by weight indicated below, was mixed in a vessel to obtain a generally random mixture of the ingredients:

| | |
|---|---|
| citric acid | 94% |
| EDTA (disodium) | 4% |
| sodium lauryl sulfate | 1% |
| monosodium phosphate | 1% |

A dilute solution was produced by adding water to the mixture in the proportion of 99.2% water to 0.8% mixture by weight. The mixture was dissolved in the water to produce a stable solution. The solution prepared as set forth above was compared with bleach (NaOCl) to determine the sanitizing effectiveness of the solution. The solution was found to be more effective than a 200 parts per million solution of NaOCl and water against pseudomonas aeruqinosa, *staphylococcus aureus*, and *salmonella typhimurium* as well as *Saccharomyces bailii* yeast. The solution was also tested as a cleaner by applying it in liquid form to a surface contaminated with dried milk, and the liquid and contamination was wiped from the surface with a paper wipe. The solution was observed to have cleaned the surface of dried milk.

EXAMPLE 2

A dry mixture of citric acid, EDTA (disodium), and sodium lauryl sulfate, in the proportions by weight indicated below, was mixed in a vessel to obtain a generally random mixture of the ingredients:

| | |
|---|---|
| citric acid | 94% |
| EDTA (disodium) | 4% |
| sodium lauryl sulfate | 2% |

A dilute solution was produced by adding deionized water to the mixture in the proportion of 99.2% water to 0.8% mixture by weight. The mixture was dissolved in the water to produce a stable solution.

The solution was compared to a bleach (NaOCl) solution to determine the sanitizing effectiveness of the solution in the same manner as described with respect to Example 1. The solution of Example 2 was also found to be more effective than a 200 parts per million solution of NaOCl and water against *pseudomonas aeruqinosa, staphylococcus aureus, salmonella typhimurium* and *saccharomyces bailii*. The solution was also tested as a cleaner by applying it in liquid form to a surface contaminated with dried milk, and the liquid and contamination was wiped with a paper wipe from the surface. The solution was observed to have cleaned the surface of dried milk. It has been tested successfully as a CIP—clean in place—system in beverage lines and in dairy machines, milk shake and ice cream freezers.

EXAMPLE 3

A dry mixture of nontoxic sanitizing cleaner consisting of the mixture of Example 1 hereof was mixed with water to form a 2.0% solution. Mineral oil, glycerine, and stearyl alcohol were brought to a low heat and mixed under constant slow agitation. The 2.0% sanitizing solution was added to the heated mixture under agitation. The agitation continued until the mixture cooled to the ambient temperature.

This procedure produced an antimicrobal body lotion, in the proportions by weight indicated below:

| | |
|---|---|
| mineral oil | 40% |
| glycerine | 2% |
| stearyl alcohol | 8% |
| water | 49% |
| Sanitizing cleaner compostion | 1% |

Cetyl alcohol may be substituted for stearyl alcohol in the above mixture. Also, a perfume may be added, to the desired aroma level, to give the lotion a desired scent.

The lotion produced by the above-disclosed process possesses all of the sanitizing effectiveness of the solution of Example 1. This lotion, however, has the added benefit of being an effective moisturizer.

EXAMPLE 4

A dry mixture of nontoxic sanitizing cleaner consisting of the mixture of Example 2 hereof was mixed with water to form a 2.3% solution. Mineral oil, olive oil. stearyl alcohol and triethanolamine were mixed together and heated to 140 degrees Fahrenheit under agitation The 2.3% sanitizing solution was added to the heated, agitated mixture. The resultant mixture was allowed to cool slowly to the ambient temperature.

This procedure produced an antimicrobial hand lotion, in the proportions by weight indicated below:

| | |
|---|---|
| mineral oil | 42.0% |
| olive oil | 4.0% |
| stearyl alcohol | 8.0% |
| triethanolamine | 0.05% |
| water | 44.95% |
| sanitizing cleaner composition | 1.0% |

The lotion produced by the above-disclosed process possesses all of the sanitizing effectiveness of the solutions disclosed in Example 1 and Example 2. This lotion, however, has the added benefit of being an effective moisturizer.

It has been found that a solution of water and a mixture of an organic acid, chelating agent, and surfactant will be an effective sanitizer if the mixture is at least 0.8% of the solution and the water is not more than 99.2% of the solution by weight. Preferably, the solution of water and a mixture of organic acid, chelating agent, and surfactant contains between about 1% and 5% mixture to between about 99% and 95% water by weight. If a buffering agent, such as monosodium phosphate, is an ingredient of the mixture, the same ratio of mixture to water by weight applies.

The ingredients in the mixture by weight must be within the following ranges:

| | |
|---|---|
| citric acid | 90% to 98% |
| EDTA, or its salts | 2% to 10% |
| sodium lauryl sulfate | 0.5% to 2% |
| monosodium phosphate | 0% to 2% |

A preferred mixture is as follows:

| | |
|---|---|
| citric acid | 94% |
| EDTA, tetra sodium | 4% |
| sodium lauryl sulfate | 1% |
| monosodium phosphate | 1% | and this mixture is preferably mixed with 98% deionized or distilled water by weight to form a 2% solution. A 2% solution has been found to be effective as a sanitizer and cleaner of hard surfaces. In addition, this mixture can be incorporated in a water based lotion with the ingredients constituting 2% of the total and the lotion constituting 98% of the total by weight.

The inventor has found that by blending dry ionizing salts, such as sodium chloride or potassium chloride, with the dry ingredients of the nontoxic sanitizing cleaner, such as a dry powder blend, when added to ordinary tap water, acquires an increased solubilization rate as well as a greater resistance towards precipitation over time. The added salt, sodium chloride or potassium chloride, increases the ionization potential of the solution. Ordinary tap water can vary greatly in grains of hardness (metal salts) which may chemically tie up some of the chelation potential of the sanitizing cleaner without added salt. Therefore, the addition of ionizing salt or salts helps to prevent a completion of this chemical reaction. Also, such ionization salts have an additive effect to accelerate the killing of microorganisms.

The ratios of nontoxic sanitizing cleaner, powder form, to salt, either sodium or potassium chloride, can be varied and is effective as such ratios 1:1, 2:1, 1:2, and 1:3. These are the preferable ratios, other ratios can also be effective depending on the hardness of the water.

Preferred Ratios of Dry Ingredients

| Water Grains of Hardness | Nontoxic Sanitizing Cleaner | | salt, sodium and/or potassium chloride |
|---|---|---|---|
| Less than 8.0 | 2 | to | 1 |
| 8.0 to 10.0 | 1 | to | 2 |
| 10.0 to 25.0 | 1 | to | 2 |
| 25.0 plus | 1 | to | 3 plus |

The addition of salt, sodium chloride or potassium chloride, to the sanitizing cleaner blend is preferred when using tap water (ordinary) rather than deionized or distilled water in any of the examples.

An aqueous solution of the sanitizing cleaner of the present invention contains only chemicals which may be added to foods for human consumption, namely, ingredients that are produced to meet the specifications of the Food Chemicals Codex III and the United States Pharmacopeia XXII, and accordingly do not present a health hazard even if small amounts of the solution are ingested. Because of this fact, surfaces may be cleaned by applying an aqueous solution of the sanitizing cleaner of the present invention and the residue left on the surface. In like manner, a solution of the sanitizing cleaner of the present invention may be utilized to clean in place food processing or dispensing equipment, such as milk processing equipment, beer dispensing systems, soft drink dispensing systems, milk dispensing equipment and soft ice cream or yogurt dispensing equipment.

Conventionally, beer and soft drink dispensing equipment is designed to use the beer or drink mixture in the container used to transport the product to the vendor or user. The container is stored in an out of the way location, and connected to a delivery or discharge spout by piping and a valve located at the spout. The dispersing equipment has some means for transporting the liquid product from the container to the spout, such as a pump or a source of pressurized gas. With beer and soft drinks, the means to transport the product is generally a pressurized container of carbon dioxide connected to the top of the source container, the beer or soft drink being withdrawn from the lower portion of the container below the surface of the liquid product as a result of the pressure of the carbon dioxide gas on the surface of the liquid. Soft ice cream or yogurt generally uses a pump with an inlet tube extending below the surface of the product and an outlet connected to the piping. Milk processing equipment generally employs a pump with an inlet connected to an opening at the bottom of the source container, and an outlet connected to the piping. In the case of milk, the piping may include heat exchangers to raise or lower the temperature of the product and/or homogenizers.

Some equipment for dispersing food or drink for human consumption has an integral air-tight sealed container adapted to contain a body of liquid for human consumption, and piping means extending from the container to the location the liquid is to be discharged. The equipment also has a valve controlled discharge opening connected to the piping means and disposed at the discharge location, and means associated with the container for moving the contents of the container from the container, through the piping means to the valve and discharge opening.

Such food processing equipment and drink dispensing equipment must be cleaned in place on a regular schedule to prevent the buildup of microorganisms within the equipment. The conventional process for cleaning in place such equipment has been to first drain the equipment of all product, then circulate a strong sanitizing liquid, such as a solution based on chlorine, iodine or a quaternary compound, through the equipment, thereafter rinsing the equipment by circulating water through the equipment, and thereafter returning the liquid product to be processed or dispensed to the container therefor. Generally, this process must be carried out by specially trained personnel because of the danger in handling the sanitizing preparation and the care required in completing the process.

Such food processing equipment or drink dispensing equipment may be cleaned in place and simultaneously sanitized using an aqueous solution of the sanitizing preparation of the present invention omitting the follow up rinse of the equipment, and the cleaning and sanitizing process may be conducted by less skilled personnel than required for the process of the prior art, with less danger of accident, and in less time. Further, the inventor's tests show that using an aqueous solution of the sanitizing preparation of the present invention to clean in place such processing or dispensing equipment is likely to produce a greater microorganism kill than the processes of the prior art.

When cleaning a drink dispenser installation, a tank of an aqueous solution of the sanitizing composition of the present invention is connect to the system in place of the container for the product to be dispensed. In a preferred process, the solution contains about 98% water and about 2% by weight composition. The composition consists of 94% citric acid, 4% EDTA, 1% sodium laurel sulfate, and 1% monosodium phosphate, by weight. A pump and a first hose are provided and connected between the tank of aqueous solution and one end of the piping of the drink dispenser. A second hose is connected between the spout and the tank. The pump is activated for a period of time to circulate the aqueous solution through out the piping, valve and spout of the drink dispensing equipment. The period of circulation time required is that required to clean the piping, valve and spout of the drink dispensing equipment and to kill those microorganisms which are responsive to the solution, generally a period of three to five minutes. Thereafter, the pump is deactivated, the first and second hoses removed, and the piping, spout and valve drained of excess solution. The system is not rinsed. Thereafter, the tank of solvent is removed and a container of the liquid drink product is connected to the piping in the conventional manner. The valve is opened to permit a small quantity of the liquid product to be dispensed to flow from the spout, taking with it much of the cleaning and sanitizing solution left in the piping, valve and spout after draining the solvent therefrom. The valve is then closed, and the portion of the liquid product removed from the piping, valve and spout after draining the cleaning and sanitizing solution from said system, is discarded. The dispensing system is now ready to dispense the liquid product in the container, and small traces of the cleaning and sanitizing solution can be ingested by humans, since it consists of recognized food additives.

In equipment in which the container and piping are an integral assembly, the container is emptied of its liquid food or beverage contents, except for the portion that adheres to surfaces, and a body of the solution of the present invention is placed in the container. Thereafter, the valve at the discharge opening is opened and the means for moving the body of solution in the container is actuated to cause the liquid body to flow from the container, through the piping means to the valve and discharge opening, thereby transferring the body of solution from the container and through the discharge opening, except for a portion that adheres to surfaces. The portion of the body of solution that remains on the surfaces of the container and piping means is permitted to remain within the liquid dispensing device. Thereafter, a new body of the liquid food or drink for ingestion is placed within the container, and an initial portion of the liquid food or beverage is dispensed from the equipment and discarded. The remaining portion of the liquid food or beverage is thereafter dispensed from the equipment for human consumption even though it contains traces of the solution used to sanitize the equipment.

Those skilled in the art will recognize other applications for the present invention and other forms of the present invention. Therefore, it is intended that the present invention be limited not by the foregoing specification, but rather by the appended claims.

The invention claimed is:

1. A solution that is noncaustic and safe to apply to food contacting surfaces, is effective to kill microorganisms on said surfaces, and facilitates wiping soil and dead microorganisms from said surfaces consisting essentially of a composition and water, said composition consisting essentially of between about 85% and 98% of at least one acid, all acid of the composition being organic and selected from the group consisting of citric acid, fumaric acid, tartaric acid, malic acid, lactic acid and adipic acid, and mixtures thereof, between about 0.2% and 10% of a chelating agent selected from the group consisting of ethylenediaminetetraacetic acid (EDTA) and its salts, salicylic acid, polyphosphates, ascorbic acid and mixtures thereof, and between about 0.2% and 5.0% of a surfactant selected from the group consisting of sodium lauryl sulfate, ammonium lauryl sulfate, a sarcosinate, a sulfosuccinate, and mixtures thereof, by weight, the solution having a pH less than 3 and being noncaustic and nontoxic.

2. A solution that is noncaustic and safe to apply to food contacting surfaces, is effective to kill microorganisms on said surfaces, and facilitates wiping soil and dead microorganisms from said surfaces consisting essentially of water and a composition, said composition consisting essentially of between about 85% and 98% of at least one acid, all acid of the composition being organic and selected from the group consisting of citric acid, fumaric acid, tartaric acid, malic acid, lactic acid and adipic acid, and mixtures thereof, between about 0.2% and 10% of a chelating agent selected from the group consisting of ethylenediaminetetraacetic acid (EDTA) and its salts, salicylic acid, polyphosphates, ascorbic acid and mixtures thereof, and between about 0.2% and 5.0% of a surfactant selected from the group consisting of sodium lauryl sulfate, ammonium lauryl sulfate, a sarcosinate, a sulfosuccinate, and mixtures thereof by weight, and a buffering agent, the buffering agent being between about 0.2% and 5.0% of the composition by weight, and being selected from the group consisting of monosodium phosphate, potassium phosphate and mixtures thereof, the composition having a pH less than 3, whereby the solution is noncaustic and nontoxic.

3. A solution that is noncaustic and safe to apply to food contacting surfaces, is effective to kill microorganisms on said surfaces, and facilitates wiping soil and dead microorganisms from said surfaces consisting essentially of claim 1 wherein the organic acid consists of citric acid.

4. A solution that is noncaustic and safe to apply to food contacting surfaces, is effective to kill microorganisms on said surfaces, and facilitates wiping soil and dead microorganisms from said surfaces consisting essentially of a solution of claim 1, wherein the water constitutes between about 95% and 99.8% of the solution by weight.

5. A solution that is noncaustic and safe to apply to food contacting surfaces, is effective to kill microorganisms on said surfaces, and facilitates wiping soil and dead microorganisms from said surfaces consisting essentially of claim 4 wherein the organic acid consists of citric acid.

6. A solution that is safe to apply to food contacting surfaces, is effective to kill microorganisms on said surfaces, and facilitates wiping soil and dead microorganisms from said surfaces consisting essentially of claim 5 wherein the chelating agent consists of EDTA or its salts.

7. A solution that is safe to apply to food contacting surfaces, is effective to kill microorganisms on said surfaces, and facilitates wiping soil and dead microorganisms from said surfaces consisting essentially of claim 4 wherein the surfactant consists of sodium lauryl sulfate.

8. A solution that is noncaustic and safe to apply to food contacting surfaces, is effective to kill microorganisms on said surfaces, and facilitates wiping soil and dead microorganisms from said surfaces consisting essentially of the solution of claim 2, the water constituting between about 95% and 99.5% of the solution by weight.

9. A solution that is noncaustic and safe to apply to food contacting surfaces, is effective to kill microorganisms on said surfaces, and facilitates wiping soil and dead microorganisms from said surfaces consisting essentially of claim 2 wherein the buffering agent consists of monosodium phosphate.

10. A solution that is noncaustic and safe to apply to food contacting surfaces, is effective to kill microorganisms on said surfaces, and facilitates wiping soil and dead microorganisms from said surfaces consisting essentially of claim 4 wherein the composition consists of 94% citric acid, 4% EDTA or its salts, and 2% sodium lauryl sulfate, by weight.

11. A solution that is noncaustic and safe to apply to food contacting surfaces, is effective to kill microorganisms on said surfaces, and facilitates wiping soil and dead microorganisms from said surfaces consisting essentially of a composition and water, the composition consisting essentially of 94% citric acid, about 4% ethylenediaminetetraacetic acid (EDTA) or its salts, about 1% sodium lauryl sulfate, and about 1% monosodium phosphate, by weight, the solution having a pH less than 3, the solution containing about 2% composition and about 98% water, by weight and being noncaustic and nontoxic.

12. A sanitizing hand lotion consisting essentially of claim 8 in combination with a water based lotion, the water of the lotion forming a solution with the composition and being equal to about 98% of the composition by weight.

13. The method of sanitizing and cleaning a surface of microorganisms and dirt consisting essentially of applying to the surface a solution according to claim 4, thereby forming a liquid body on said surface containing solution, dirt and microorganisms, thereafter wiping the surface with an absorbent material to divide the body into two portions, one portion of the body being absorbed in the absorbent material and the other portion remaining on the surface, removing the absorbent material with the absorbed one portion of the liquid body and dead microorganisms and dirt from the surface, and thereafter permitting the second portion of the liquid body to remain on the surface for a period of time sufficient to kill additional microorganisms.

14. The method of sanitizing and cleaning a surface of microorganisms and dirt thereon consisting essentially of applying to the surface a solution according to claim 6, thereby forming a liquid body on said surface containing solution, dirt and microorganisms, thereafter wiping the surface with an absorbent material to divide the body into two portions, one portion of the body being absorbed in the absorbent material and the other portion remaining on the surface, removing the absorbent material with the absorbed one portion of the liquid body and dead microorganisms and dirt from the surface, and thereafter permitting the second portion of the liquid body to remain on the surface for a period of time sufficient to kill additional microorganisms.

15. The method of sanitizing and cleaning a surface of microorganisms and dirt consisting essentially of applying to the surface a solution according to claim 8, thereby forming a liquid body on said surface containing solution, dirt and microorganisms, thereafter wiping the surface with an absorbent material to divide the body into two portions, one portion of the body being absorbed in the absorbent material and the other portion remaining on the surface, removing the absorbent material with the absorbed one portion of the solution and dead microorganisms and dirt from the surface, and thereafter permitting the second portion of the liquid body to remain on the surface for a period of time sufficient to kill additional microorganisms.

16. The method of sanitizing and cleaning a surface consisting essentially of applying to the surface a solution according to claim 11, thereby forming a liquid body on said surface containing solution, dirt and microorganisms, thereafter wiping the surface with an absorbent material to divide the body into two portions, one portion of the body being absorbed in the absorbent material and the other portion remaining on the surface, removing the absorbent material with the absorbed one portion of the solution and dead microorganisms and dirt from the surface, and thereafter permitting the second portion of the solution to remain on the surface for a period of time sufficient to kill additional microorganisms.

17. A solution that is noncaustic and safe to apply to food contacting surfaces, is effective to kill microorganisms on said surfaces, and facilitates wiping soil and dead microorganisms from said surfaces, said solution consisting essentially of a composition and water, said composition consisting essentially of between about 90% and 98% of at least one acid, all acid of the composition being organic and selected from the group consisting of citric acid, fumaric acid, tartaric acid, malic acid, lactic acid and adipic acid, and mixtures thereof, between about 2% and 10% of a chelating agent selected from the group consisting of ethylenediaminetetraacetic acid (EDTA) and its salts, salicylic acid, polyphosphates, ascorbic acid and mixtures thereof, and between about 0.5% and 2% of a surfactant selected from the group consisting of sodium lauryl sulfate, ammonium lauryl sulfate, a sarcosinate, a sulfosuccinate, and mixtures thereof, by weight, the solution having a pH less than 3 and being noncaustic and nontoxic.

18. A solution that is noncaustic and safe to apply to food contacting surfaces, is effective to kill microorganisms on said surfaces, and facilitates wiping soil and dead microorganisms from said surfaces consisting essentially of a composition and water, the composition consisting essentially of between about 90% and 98% of at least one acid, all acid of the composition being organic and selected from the group consisting of citric acid, fumaric acid, tartaric acid, malic acid, lactic acid and adipic acid, and mixtures thereof, between about 2% and 10% chelating agent selected from the group consisting of ethylenediaminetetraacetic acid (EDTA) and its salts, salicylic acid, polyphosphates, ascorbic acid and mixtures thereof, between about 0.5% and 2% surfactant selected from the group consisting of sodium lauryl sulfate, ammonium lauryl sulfate, a sarcosinate, a sulfosuccinate, and mixtures thereof by weight, and a buffering agent, the buffering agent being between about 0% and 2% of the composition by weight, and being selected from the group consisting of monosodium phosphate, potassium phosphate and mixtures thereof, the solution having a pH less than 3 and being noncaustic and nontoxic.

19. A solution that is noncaustic and safe to apply to food contacting surfaces, is effective to kill microorganisms on said surfaces, and facilitates wiping soil and dead microorganisms from said surfaces consisting essentially of a composition and water, said composition consisting essentially of between about 90% and 96% citric acid, between about 0.2% and 10% ethylenediaminetetraacetic acid (EDTA) and its salts, and between about 0.5% and 2.0% sodium lauryl sulfate, by weight, the solution having a pH less than 3 and being noncaustic and nontoxic.

20. A solution that is noncaustic and safe to apply to food contacting surfaces, is effective to kill microorganisms on said surfaces, and facilitates wiping soil and dead microorganisms from said surfaces consisting essentially of a solution of claim 19, and between about 0.5% and 2.0% monosodium phosphate by weight.

21. A solution that is noncaustic and safe to apply to food contacting surfaces, is effective to kill microorganisms on said surfaces, and facilitates wiping soil and dead microorganisms from said surfaces consisting essentially of a solution of claim 19, wherein the water constitutes about 98% of the solution by weight.

* * * * *